(12) United States Patent
Connolly et al.

(10) Patent No.: US 8,435,779 B2
(45) Date of Patent: May 7, 2013

(54) PROCESS FOR PRODUCING A VIRUS-INACTIVATED THROMBIN PREPARATION

(75) Inventors: Caroline Connolly, Glasgow (GB); Christopher Hardway, Watford (GB); David Evans, Bushey (GB); Peter Feldman, Stanmore (GB)

(73) Assignee: Bio Products Laboratory Limited, Hertfordshire (GB)

( * ) Notice: Subject to any disclaimer, the term of this patent is extended or adjusted under 35 U.S.C. 154(b) by 1575 days.

(21) Appl. No.: 10/520,457

(22) PCT Filed: Jul. 7, 2003

(86) PCT No.: PCT/GB03/02942
§ 371 (c)(1),
(2), (4) Date: Nov. 30, 2005

(87) PCT Pub. No.: WO2004/007707
PCT Pub. Date: Jan. 22, 2004

(65) Prior Publication Data
US 2006/0134769 A1    Jun. 22, 2006

(30) Foreign Application Priority Data
Jul. 10, 2002 (GB) .................. 0216002.6

(51) Int. Cl.
*C12N 9/74* (2006.01)
(52) U.S. Cl.
USPC .......................................... 435/214; 435/183
(58) Field of Classification Search ............ None
See application file for complete search history.

(56) References Cited

U.S. PATENT DOCUMENTS

| 5,143,838 A | 9/1992 | Kraus et al. |
| 5,304,372 A | 4/1994 | Michalski et al. |
| 5,354,682 A * | 10/1994 | Kingdon et al. ............. 435/214 |
| 5,714,370 A | 2/1998 | Eibl et al. |
| 5,723,123 A * | 3/1998 | Karges et al. ............. 424/94.64 |
| 5,907,032 A | 5/1999 | MacGregor et al. |
| 6,245,548 B1 * | 6/2001 | Ralston et al. ............. 435/214 |
| 6,346,277 B1 * | 2/2002 | Heimburger et al. ......... 424/530 |
| 7,351,561 B2 * | 4/2008 | Metzner et al. ............. 435/183 |
| 2003/0133829 A1 * | 7/2003 | Anderle et al. .............. 422/28 |

FOREIGN PATENT DOCUMENTS

| EP | 0 439 156 A1 | 7/1991 |
| EP | 0 543 178 A2 | 5/1993 |
| EP | 0 565 511 A1 | 10/1993 |
| EP | 1 136 084 A1 | 2/2001 |
| EP | 1 161 958 A1 | 12/2001 |
| JP | 05194261 A2 | 8/1993 |
| WO | WO 00/71153 A2 | 11/2000 |

OTHER PUBLICATIONS

Piet et al., "The use of tri(n-butyl) phosphate mixtures to inactivate hepatitus viruses and human immunodeficiency virus in plasma and plasma's subsequent fractionation", Transfusion, 1990, vol. 30, pp. 591-598.*
Goldsack, N.R. et al. (1998) "Molecules in focus thrombin" The International Journal of Biochemistry & Cell Biology 30:641-646.
Feldman, P.A. et al. 1994 "Large-scale preparation and biochemical characterization of a new high purity factor IX concentrate prepared by metal chelate affinity chromatography" *Blood Coagulation and Fibrinolysis* 5:939-948.

* cited by examiner

*Primary Examiner* — Laura Schuberg
(74) *Attorney, Agent, or Firm* — Knobbe Martens Olson & Bear LLP

(57) ABSTRACT

The present invention relates to processes for the preparation of virus inactivated thrombin, and to the products prepared by these processes.

23 Claims, No Drawings

PROCESS FOR PRODUCING A VIRUS-INACTIVATED THROMBIN PREPARATION

RELATED APPLICATIONS

This application is a U.S. National Phase under 35 U.S.C. 371 of International Application No.: PCT/GB2003/002942, filed Jul. 7, 2003 designating the U.S. and published in English on Jan. 22, 2004 as WO 2004/007707, which claims the benefit of British patent application No. GB 0216002.6, filed Jul. 10, 2002.

FIELD OF INVENTION

The present invention relates to processes for the preparation of virus inactivated thrombin, and to the products prepared by these processes.

BACKGROUND OF THE INVENTION

Thrombin is a multifunctional plasma protease generated in the blood stream through activation of its inactive precursor, prothrombin (also known as factor II). Prothrombin is itself activated by the action of activated factor X (factor Xa). One of the main functions of thrombin in blood plasma is to convert soluble fibrinogen into insoluble fibrin in the final step of the blood clotting cascade. The fibrin monomers produced by the action of thrombin cluster together and are then cross linked to form a blood clot. Thrombin is used in therapy both alone and in combination with fibrinogen in the so-called fibrin sealants to achieve haemostasis, to seal wounds and for the controlled adhesion of tissue.

For all clinical applications, it is important to have highly pure thrombin in order to minimise any undesirable side effects resulting from, for example, the presence of other proteases or clotting factors, or other contaminating components. In addition, it is highly desirable that thrombin for clinical use, in particular if it is derived from human or animal sources, is treated to inactivate any blood-borne viruses which may be present, for example hepatitis viruses or HIV. Various methods of virus inactivation are known in the art, including pasteurisation, dry heat treatment and solvent-detergent treatment (Pathogen Inactivation of labile blood products, Council of Europe Expert Committee in Blood Transfusion Study Group on Pathogen Inactivation in Labile Blood Products, *Transfusion Medicine*, 2001, 11, 149-175). It is also desirable that other pathogens are removed or reduced, for example the causative agents of Transmissible Spongiform Encephalopathies (TSE), currently believed to be prions.

Dry heat treatment is known to be effective for the inactivation of both enveloped and some non-enveloped viruses, whilst solvent-detergent treatment is known to be effective for the inactivation of enveloped (i.e. lipid coated) viruses such as hepatitis B. Solvent-detergent treatment is now a commonly used method for virus inactivation of blood products intended for clinical use.

In the past, the activation of prothrombin to thrombin was often brought about by the addition of calcium ions and thromboplastin (factor III). The thromboplastin would be derived from human or animal sources and was therefore a source of possible contamination of the final product.

U.S. Pat. No. 5,304,372 discloses a process for the preparation of a human thrombin concentrate from the PPSB fraction of plasma. The process comprises activation of the prothrombin in the PPSB fraction to produce thrombin by the addition of calcium chloride, followed by solvent-detergent treatment on the resulting product to inactivate viruses. According to U.S. Pat. No. 5,304,372 the solvent-detergent treatment cannot be carried out on the PPSB starting material because it would eliminate other factors such as phospholipids necessary for the activation reaction of prothrombin to thrombin.

EP-A-0,378,798 discloses a process for the preparation of thrombin which comprises absorbing factor II from plasma or plasma fractions onto a solid carrier,. activating the factor II on the solid carrier to thrombin and then eluting the thrombin.

U.S. Pat. No. 5,714,370 discloses the preparation of thrombin from virus-inactivated prothrombin using coagulatively active salts to effect the activation of the prothrombin to thrombin. The only method disclosed for the virus-inactivation of the prothrombin is heat treatment.

The 1993 Annual Report of the Dr. Karl Landsteiner Foundation on research at CLB (the Central Laboratory of the Netherlands Red Cross blood transfusion service) also reported on page 10 that activation of solvent-detergent treated prothrombin to form thrombin with calcium ions was only successful in the presence of added phospholipids.

It would be advantageous to provide a method for the preparation of thrombin from prothrombin which has undergone a solvent-detergent virus inactivation step to remove enveloped viruses. It would also be advantageous to avoid completely the use of other biological and particularly animal-derived products, for example thromboplastin, to activate the prothrombin, as such products may serve as a source of infectious viruses or other undesirable contaminants during the manufacturing process.

SUMMARY OF THE INVENTION

In one aspect, the present invention therefore provides a first method for the preparation of virus-inactivated thrombin comprising the steps of:

(a) solvent-detergent virus inactivation of a solution comprising prothrombin and factor X;

(b) loading the product of step (a) onto an anion exchange medium;

(c) washing the medium to remove the reagents used for the solvent-detergent virus inactivation in step (a); and (d) activating the prothrombin on the medium to form thrombin by the addition of metal ions. Preferably the metal ions are divalent metal ions such as magnesium and/or calcium ions.

Preferably, the thrombin is then selectively eluted from the anion exchange medium.

Alternatively, a solution comprising prothrombin and factor X can be loaded onto an anion exchange medium and solvent-detergent virus inactivation carried out on the medium. The present invention therefore also provides an alternative to the above method wherein steps (a) and (b) are replaced by steps (a') and (b'):

(a') loading a solution comprising prothrombin and factor X onto an anion exchange medium; and (b') solvent-detergent virus inactivation of the prothrombin and factor X on the medium. The remaining steps of this alternative method are identical to the remaining steps of the first method described above. The method comprising steps (a) and (b) is preferred over the method comprising steps (a') and (b'), as it is easier to verify attainment of the necessary inactivation conditions prior to loading onto the medium.

DETAILED DESCRIPTION OF THE PREFERRED EMBODIMENT

The starting material for the process of the invention may be any solution which comprises prothrombin and factor X, including plasma fractions or prothrombin and/or factor X derived by gene expression for example in cell culture or transgenic species, and prothrombin and/or factor X produced by any other synthetic methods. The starting material may be prepared by any suitable method known in the art. Preferably, the starting material is a prothrombin complex or a derivative thereof which contains both prothrombin and factor X. Prothrombin complex may be prepared by methods known in the art, for example by adsorption onto anion exchange media from cryoprecipitate supernatant and subsequent elution (P. A. Feldman, L. Harris, M. E. Haddon, D. R. Evans and J. K. Smith, Thrombosis Research, 1986, Supplement VI:36, incorporated by reference). In a preferred embodiment, the starting material is prothrombin complex concentrate (PCC) which has been prepared under conditions which minimise the level of coagulation factor VII and activated coagulation factors in the prothrombin complex. The so-called "three-factor PCC" is therefore a more preferred starting material than "four-factor PCC".

The solvent-detergent virus inactivation step is carried out using reagents and methods known in the art (see for example U.S. Pat. Nos. 4,481,189, 4,613,501 and 4,540,573, all incorporated by reference). Suitable solvents include tri-n-butylphosphate (TNBP). Suitable detergents include polysorbate (Tween) 80, polysorbate (Tween) 20 and Triton X-100. A particularly preferred combination is polysorbate 80 and TNBP. In a preferred embodiment, the prothrombin and factor X-containing solution is stirred with the solvent and detergent reagents. The virus inactivation is carried out at a temperature and for a time sufficient to inactivate any enveloped viruses that may be present. For example, the solvent-detergent treatment may be carried out for from about 1 to about 24 hours, at a temperature of from about 4° to about 37° C., for example at least about 6 hours at a temperature of about 23-27° C.

The solvent-detergent treated prothrombin and factor X containing solution is then loaded onto a suitable anion exchanger under conditions such that the prothrombin and factor X bind to the anion exchange media. If necessary, the solvent-detergent treated solution is first diluted to reduce the ionic strength to one that is suitable for binding of the prothrombin and factor X onto the anion exchanger. Suitable anion exchange media are available commercially, and include DEAE Sepharose CL6B supplied by Amersham Biosciences and Fractogel EMD DEAE 650(S) supplied by Merck. Preferably, the anion exchange medium is present in a column to facilitate washing and elution. Preferably, if an anion exchange medium was used during the preparation of the starting material, for example for the capture of prothrombin and/or factor X from a source material such as plasma, then the same anion exchange medium is used for the process of the invention in order to minimise exposure to different reagents.

After loading, the anion exchange medium is washed with one or more suitable washing buffers to remove unbound or loosely bound protein and the solvent-detergent reagents. The washing buffers should be free of reagents which may generate thrombin from the bound prothrombin.

The bound prothrombin is then activated to form thrombin by the addition of suitable metal ions, preferably divalent metal ions such as magnesium or calcium ions, most preferably calcium ions. Combinations of more than one type of metal ion may be used for the activation, for example a mixture of calcium and magnesium ions. Preferably, the metal ions are added in the form of an activation buffer and are present in a concentration of between about 1 and about 40 mM, more preferably between about 1.5 and about 17 mM, and most preferably about 2 mM in the buffer.

The bound prothrombin is incubated with the metal ions for a sufficient time and at a suitable temperature for the activation reaction to proceed. The temperature should be high enough for the reaction to proceed but not so high that the proteins present are denatured or any contaminating microorganisms are encouraged to grow. The reaction is preferably carried out at or below about 26° C., for example at 10°-26° C., more preferably at about room temperature (20° C.) or below, for about 19-85 hours, more preferably 19-65 hours and even more preferably for about 40-65 hours. For example, suitable incubation conditions might be for about 65 hours at about 20° C.

Without wishing to be bound by any theory, it is believed that it is the combination of the metal (e.g. calcium) ions and the anion exchange medium to which the prothrombin is bound which allows activation of the prothrombin to form thrombin without the need for addition of any further activating agents, for example thromboplastin. The metal ions activate factor X in the adsorbed fraction to form factor Xa, and the factor Xa in turn activates the prothrombin to form thrombin. It is also possible to load solvent-detergent virus inactivated factor X onto the anion exchange medium and to activate it to form factor Xa by addition of metal ions before the prothrombin is added to the anion exchange medium. The factor Xa then converts the prothrombin to thrombin on the medium.

The present invention therefore also provides a second method for the preparation of virus-inactivated thrombin comprising the steps of:

(a) solvent-detergent virus inactivation of a solution comprising factor X;

(b) loading the product of step (a) onto an anion exchange medium;

(c) washing the medium to remove the reagents used for the solvent-detergent virus inactivation in step (a);

(d) activating the factor X on the medium to form factor Xa by the addition of metal ions; and (e) loading virus-inactivated prothrombin onto the anion exchange medium such that thrombin is generated.

Preferably, the thrombin is then selectively eluted from the anion exchange medium. Also preferably the metal ions are divalent metal ions such as magnesium and/or calcium ions.

The starting material for the second process of the invention may be any solutions which separately comprise prothrombin and factor X, including plasma fractions, prothrombin and/or factor X derived by gene expression, for example in cell culture or transgenic species, and prothrombin and/or factor X produced by any other synthetic methods. The starting materials may be prepared by any suitable method known in the art. Suitable virus-inactivation, loading and activation conditions for the second method of the invention are as described above for the first method of the invention.

After the activation of factor X to form factor Xa, the anion exchange medium may optionally be washed using a suitable buffer to remove the metal ions before the prothrombin is added.

Following the conversion of prothrombin to thrombin, the thrombin may be recovered by elution with a suitable recovery buffer. The ionic strength and pH of the recovery buffer are preferably chosen to selectively remove the thrombin and to leave other proteins, for example any unconverted prothrombin, bound to the anion exchange medium. The pH of the recovery buffer used should be below the pI of thrombin such that the thrombin does not bind to the anion exchanger. A suitable pH for the recovery buffer is pH 8. Preferably, the buffers used for washing, activation and recovery do not contain any phosphate salts, in order to avoid precipitation of insoluble calcium phosphate during the manufacturing process.

The thrombin produced is highly purified and concentrated and may be formulated directly without further purification. Alternatively, further purification steps may be carried out if desired. For example, the thrombin solution obtained from the anion exchanger media may be subjected to further virus reduction or inactivation steps. For example, the solution may be filtered through a virus removal filter such as a Planova 15N filter. Such filtration may also serve to remove the causative agent of Transmissible Spongiform Encephalopathies (TSE).

Once separated from the anion exchange medium, the thrombin product may be formulated for long term storage before clinical use. Preferably, the thrombin solution is freeze-dried, optionally in the presence of one or more stabilisers to help limit denaturation during freeze drying and any subsequent heat treatment. Suitable stabilizers include carbohydrates such as sucrose, raffinose or trehalose and divalent metal ions such as calcium ions. Particularly preferred are a combination of calcium ions and a carbohydrate such as sucrose. Preferably, the use of protein stabilisers such as albumin is avoided so as to minimise possible sources of contamination in the final product.

Suitable freeze drying conditions include primary drying at a temperature of about −35° C. and a pressure of about 100-130 microbar (10-13 Pa), followed by secondary drying at a temperature of about +35° C. and a pressure of about 30 microbar (3 Pa).

The freeze-dried thrombin product may be subjected to a further virus inactivation step by heat-treatment, for example heating to about 80° C. for about 72 hours or 100° C. for 24 hours. A combination of calcium ions and a carbohydrate such as sucrose has been found to efficiently stabilise thrombin produced according to the invention during terminal heat treatment to inactivate viruses.

It is desirable for blood-derived products to undergo at least two separate virus inactivation or reduction steps during manufacture. An advantage of the process of the invention is that it allows multiple different virus inactivation or reduction steps to be carried out, in order to inactivate or reduce both enveloped and non-enveloped viruses, and other pathogens, for example the causative agents of TSE. Solvent-detergent treatment is known to disrupt the lipid envelope of enveloped viruses, whilst filtration separates out particles over a certain size and heat treatment inactivates thermally unstable viruses. It is desirable to incorporate multiple inactivation or reduction steps which are based on different principles, in order to remove or reduce as many different pathogens as possible. In a preferred embodiment, the process comprises a further virus inactivation or reduction step in addition to the solvent-detergent treatment. In a more preferred embodiment, the process comprises two further virus reduction or inactivation steps in addition to the solvent-detergent treatment. Preferably, the process comprises a physical virus removal step (e.g. nanofiltration) and a dry heat virus inactivation step in addition to the solvent-detergent treatment.

Another advantage of the process of the invention is that activation of the prothrombin and purification of the resulting thrombin may be achieved using the same type of anion exchange medium as was used previously to prepare the prothrombin and factor X starting material. Formulation of the product also utilizes reagents which have already been used in the preparative process. This minimizes the exposure of the thrombin to a multiplicity of reagents, which is beneficial in the manufacture of a pharmaceutical product. A further advantage of the process is that it minimises the threat to the integrity of other manufacturing operations posed by possible contact with the highly potent thrombin protease. This can be avoided normally only by segregation of the thrombin manufacturing plant from other equipment and activities in the factory. Such segregation is expensive and labour intensive. Also, processing of virus-inactivated (e.g. solvent-detergent treated) intermediates has to be done in a separates isolated manufacturing area to avoid any subsequent contamination. The prior art inability to generate thrombin after solvent-detergent treatment required the use of significantly more segregated manufacturing space and additional risks in handling the product during transfer from step to step. Additionally, there was also the potential risk to manufacturing staff from handling a protease which can have significant thrombotic effects if inadvertently introduced into their circulation. These problems are minimised by use of the process of the invention because (a) prior solvent-detergent treatment means that the generated thrombin does not need to be processed in numerous different manufacturing areas, each of which would have to be isolated from other activities;

(b) the number of manufacturing steps (particularly after generation of thrombin from prothrombin) is minimised; and (c) the yield is sufficient to provide significant quantities of thrombin from very small volumes. Thus containment of the process is greatly simplified.

It is also advantageous to limit exposure of the product to multiple different reagents during manufacture, as such reagents may serve as a source of undesirable contamination or modification of the product. Minimising the number of reagents and steps required for the manufacture of thrombin from prothrombin is a further advantage of the process of the invention.

The thrombin prepared using the process of the invention may be used clinically, either alone or in combination with fibrinogen in a fibrin sealant kit. The present invention therefore also provides thrombin obtained according to a process of the invention, for use in therapy, and pharmaceutical kits comprising thrombin obtained according a process of the invention in combination with fibrinogen. Preferred are kits comprising thrombin prepared according to a process of the invention and fibrinogen prepared according to the applicant's co-pending PCT application No. (unknown) entitled "Processes for the preparation of fibrinogen" filed on 7 Jul. 2003 claiming priority from UK patent application No. 0216001.8 filed on 10 Jul. 2002, the disclosure of which is hereby incorporated by reference.

The following is a more detailed description of preferred embodiments of the process of the invention.

Removal of Cryoprecipitate from Plasma

Frozen human plasma is conditioned at around −11° C., thawed to about +1° C. and cryoprecipitate collected by centrifugation. The supernatant is called cryoprecipitate supernatant (CPS).

Capture of Prothrombin Complex from Cryoprecipitate Supernatant

Adsorption of Prothrombin Complex from Cryoprecipitate Supernatant

Anion exchange medium, such as DEAE Sepharose CL-6B, is added to CPS in proportions of, for example, ~10 ml packed anion exchange medium per kilogram CPS. The mixture is stirred for a suitable time and then the medium (including adsorbed protein) is recovered from the CPS, for example by centrifugation.

Elution of the Prothrombin Complex

The recovered anion exchange medium is suspended in a suitable buffer and packed into a chromatography column. The medium is washed with a low salt buffer to remove loosely bound and unwanted proteins. The loading and washing conditions are controlled to specifically minimise the level of coagulation factor VII and activated coagulation factors in the eluted prothrombin complex. The medium is then washed with a high salt elution buffer to recover the prothrombin complex. The protein peak is selectively collected to avoid contamination of the prothrombin complex with activated coagulation factors. The eluate can be stored frozen.

Solvent Detergent Treatment

The prothrombin complex solution is filtered through a 0.45 μm or smaller pore size filter. Solvent-detergent reagents are then added and the mixture is stirred at a temperature and for a length of time known to inactivate any enveloped viruses that may be present.

Prothrombin Activation Chromatography

Dilution of the Solvent Detergent Treated Prothrombin Complex

The solvent detergent treated prothrombin complex is then diluted with, for example, water to reduce the ionic strength of the solution to one that is suitable for binding onto an anion exchanger.

Loading the Second Anion Exchanger

The diluted protein solution is pumped through a column containing a packed anion exchange medium. Advantageously, this can be the same medium as used for the preparation of the prothrombin and factor X from CPS or other source. Microbiological contamination during thrombin generation is minimised by suitable sanitization of the anion-exchange medium and by filtration of buffers to remove bacterial contamination (e.g. by use of 0.2 μm filters). The medium is washed with the buffer used to equilibrate the column, to remove loosely bound protein and the solvent detergent reagents, and to equilibrate the medium with buffer salts which are most favourable for subsequent processing steps. The medium is then washed with approximately 1 column volume of a buffer containing calcium, for example the equilibration buffer plus 2 mM calcium chloride.

Activation Incubation

The column outlets are clamped off and the column held at a predetermined temperature for a defined time period, for example, 65 hours at 20° C. During the incubation prothrombin is converted to thrombin.

Recovery of the Thrombin

At the end of the incubation, the column is washed with the equilibration buffer to recover the thrombin. Proteins unaffected by the activation incubation remain bound to the medium as the conditions used for this wash, in terms of pH, buffer components and ionic strength, are the same as those used for the wash after loading the column. Thrombin does not bind to anion exchangers at pHs below its pI so is washed off by the buffer. For example, at pH8 thrombin does not bind to anion exchangers but its precursor, prothrombin does bind.

The peak that is eluted is collected in fractions, the first column volumes of column effluent are of lower purity thrombin and contain most of any degraded or damaged thrombin which may be present. The following column volumes are of higher purity and if separated from the first column volumes can be used without further purification. Alternatively, all the column effluent can be collected and purified further.

Virus Filtration

A further virus reduction step can be used. The thrombin-containing column eluate can be filtered through a validated virus removal filter such as a Planova 15N filter. Such filtration may also remove or reduce other pathogens, for example the causative agents of TSE.

Formulation

The thrombin is now formulated and adjusted to its target potency for long term storage before clinical use. A recommended method is the addition of a carbohydrate, such as sucrose, and calcium, at a target sodium chloride concentration and then freeze-drying the solution. Before freeze-drying the formulated product may be filtered through a sterilizing filter (e.g. 0.2 μm filter) as required for pharmaceutical use.

Terminal Heat Treatment

The freeze-dried formulation can be terminally heat-treated to inactivate any viruses that may be present.

The thrombin prepared using the process of the invention may be used clinically, either alone or in combination with fibrinogen in a fibrin sealant kit. The present invention therefore also provides thrombin obtained according to the process of the invention, for use in therapy, and pharmaceutical kits comprising thrombin obtained according the process of the invention in combination with fibrinogen. Preferred are kits comprising thrombin prepared according to the process of the invention and fibrinogen prepared according to the applicant's co-pending United Kingdom patent application entitled "Process and Composition" filed on 10 Jul. 2002.

The invention will be further illustrated by the following non-limiting examples.

The preparation of PCC is described in: Feldman P A, Bradbury P I, Williams J D, Sims G E C, McPhee J W, Pinnell M A, Harris L, Crombie G I, Evans D R, "Large scale preparation and biochemical characterisation of a new high purity factor IX concentrate prepared by metal chelate affinity chromatography.", Blood Coagulation and Fibrinolysis 1994;5: 939-948.

The pH of solutions was adjusted using suitable concentrations of sodium hydroxide to increase the pH or hydrochloric acid to reduce the pH.

Thrombin was measured by clotting assay which measures time to clot a sample of fibrinogen and/or by chromogenic assay which measured absorbance of a chromophore released by thrombin-mediated cleavage of a synthetic peptide. Such assay methods are known to those skilled in the art.

Thrombin Clotting Assay

The standard is calibrated versus an internationally accepted standard, and is diluted in assay buffer, such as 50 mM trometamol, 100 mM sodium chloride, 1% albumin, pH 7.5, to a suitable range of concentrations, for example, 1 to 7 iu/ml. The samples are diluted to within this range of concentrations.

The clotting times of the diluted thrombin solutions are measured after the addition of human fibrinogen at a fixed concentration. The relationship between test samples and the standard then allows calculation of the thrombin concentration in the sample, expressed in international units (iu) per ml.

Thrombin Chromogenic Assay

The standard is calibrated versus an internationally accepted standard, and is diluted in assay buffer, such as 50 mM trometamol, 100 mM sodium chloride, 0.1% albumin, pH 7.3, to a suitable range of concentrations, for example, 0.5 to 5 iu/ml. The samples are diluted to within this range of concentrations.

The diluted thrombin is then added to a chromogenic substrate (for example S-2238 from Chromogenix) and the mixture is incubated for a defined period of time. The reaction is then stopped by addition of, for example, acetic acid. The absorbance of the solution is then measured at 405 nm (for S-2238). The concentration of thrombin is proportional to the colour developed and the sample concentration can be interpolated from the standard line.

EXAMPLE 1

Prothrombin Activation Chromatography Trometamol Buffers and Incubation at 20° C. for 62.5 Hours 1.19 kg of solvent-detergent treated prothrombin complex was diluted with 2.50 kg of water to reduce its conductivity from 26.4 mS/cm to 9.28 mS/cm. The solution was then titrated to pH8.0. This solution was loaded onto a 5 cm diameter jacketed column packed with a 13 cm high bed of DEAE Sepharose CL6B, equilibrated with 10 mM trometamol, 110 mM sodium chloride, pH8.0. After loading the medium was washed with 15 column volumes of 10 mM trometamol, 110 mM sodium chloride, pH8.0 to remove the solvent detergent reagents and weakly bound protein. The medium was then washed with 1 column volume of 10 mM trometamol, 110 mM sodium chloride, 2 mM calcium chloride, pH8.0. The column outlets were closed. Water at 20° C. was circulated through the jacket.

After 62.5 hours, circulation of water was stopped. The medium was washed with 10 mM trometamol, 110 mM sodium chloride, pH8.0 to recover the thrombin generated during the incubation. The first 3 column volumes of column effluent which contained 3.8 million international units (iu) of thrombin clotting activity were discarded as the specific clotting activity was less than 2000 iu/mg total protein. The next 11 column volumes of effluent which contained 2.8 million iu clotting activity had a specific activity of 2400 iu/mg and were pooled for further processing, without the need for additional protein purification steps.

EXAMPLE 2

Prothrombin Activation Chromatography Citrate-Phosphate Buffers and DEAE Sepharose 4.4 kg of solvent-detergent treated prothrombin complex was diluted with 6.3 kg of water to reduce its conductivity to 9.3 mS/cm. The solution was then titrated to pH8.0. 7.1 kg of this solution was loaded onto a 9 cm diameter column packed with a 12.5 cm high bed of DEAE Sepharose CL6B, equilibrated with 8 mM citrate, 10 mM phosphate, 68.5 mM sodium chloride, pH8.0. After loading the medium was washed with 11 column volumes of 8 mM citrate, 10 mM phosphate, 68 mM sodium chloride, pH8.0 to remove the solvent detergent reagents and weakly bound protein. The medium was then washed with 1 column volume of 8 mM citrate, 10 mM phosphate, 64 mM sodium chloride, 2 mM calcium chloride, pH8.0. The column outlets were closed. The column was stored at room temperature.

After about 64 hours, the medium was washed with 8 mM citrate, 10 mM phosphate, 68 mM sodium chloride, pH8.0 to recover the thrombin generated during the incubation. A total of 11 million iu of clotting activity were recovered from the column of which 3.8 million iu had a specific activity of >2000 iu/mg and were pooled for further processing, without the need for additional protein purification steps.

EXAMPLE 3

Prothrombin Activation Chromatography Citrate-Phosphate Buffers and Fractogel EMD DEAE 650(S)

148 ml of solvent-detergent treated prothrombin complex was diluted with 121 ml of 8 mM citrate, 10 mM phosphate, pH 9.0 to reduce its conductivity to 16 mS/cm. The solution was then titrated to pH8.0. 111 g of this solution was loaded onto a 1 cm diameter column packed with 10 ml of Fractogel EMD DEAE 650(S), equilibrated with 8 mM citrate, 10 mM phosphate, 137 mM sodium chloride, pH8.0. After loading, the medium was washed with 12 column volumes of 8 mM citrate, 10 mM phosphate, 137 mM sodium chloride, pH8.0 to remove the solvent detergent reagents and weakly bound protein. The medium was then washed with 1 column volume of with 8 mM citrate, 10 mM phosphate, 129 mM sodium chloride, 2 mM calcium chloride, pH8.0. The column outlets were closed. The column was stored at room temperature.

After about 64 hours, the medium was washed with 8 mM citrate, 10 mM phosphate, 129 mM sodium chloride, 2 mM calcium chloride, pH8.0 to recover the thrombin generated during the incubation. A total of 0.4 million iu of clotting activity were recovered from the column of which 0.3 million iu had a specific activity of >2000 iu/mg and were pooled for further processing, without the need for additional protein purification steps.

EXAMPLE 4

Trometamol Buffers and Incubation at 10, 14.5 and 22° C. for About 64 Hours 195 g of solvent-detergent treated prothrombin complex was diluted with 424 g of water to reduce its conductivity from 28.9 mS/cm to 9.39 mS/cm. The solution was then titrated to pH8.0 with 1 M sodium hydroxide. About 140 g of this solution was loaded onto three 1 cm diameter jacketed columns packed with a 13 cm high bed of DEAE Sepharose CL6B, equilibrated with 10 mM trometamol, 110 mM sodium chloride, pH8.0. After loading the medium was washed with 10 column volumes of 10 mM trometamol, 110 mM sodium chloride, pH8.0 to remove the solvent detergent reagents and weakly bound protein. The medium was then washed with 1 column volume of 10 mM trometamol, 110 mM sodium chloride, 2 mM calcium chloride, pH8.0. The column outlets were closed. One column was left at room temperature (21.8° C.±0.4°). The others were maintained at 10° or 14.5° C. by circulating cooled water through the column jackets.

After about 64 hours, the temperature in the jackets was changed to 18° C. and the jacket cooling was stopped. The medium was washed with 10 mM trometamol, 110 mM sodium chloride, pH8.0 to recover the thrombin generated during the incubation. The results are shown in Table 1.

TABLE 1

| | Incubation | Thrombin clotting activity | |
|---|---|---|---|
| Column | temperature, ° C. | Total recovered, iu | Total > 2000 iu/mg, iu |
| 1 | 10 | 212,000 | 149,000 |
| 2 | 14.5 | 293,000 | 174,000 |
| 3 | 22 | 353,000 | 142,000 |

EXAMPLE 5

Trometamol Buffers and Incubation at 15, 23 and 26° C. for About 64 Hours 458 g of solvent-detergent treated prothrombin complex was diluted with 977 g of water to reduce its conductivity from 28.9 mS/cm to 9.39 mS/cm. The solution was then titrated to pH8.0 with 1 M sodium hydroxide. About 140 g of this solution was loaded onto three 1.6 cm diameter jacketed columns packed with a 13 cm high bed of DEAE Sepharose CL6B, equilibrated with 10 mM trometamol, 110 mM sodium chloride, pH8.0. After loading the medium was washed with 10 column volumes of 10 mM trometamol, 110 mM sodium chloride, pH8.0 to remove the solvent detergent reagents and weakly bound protein. The medium was then washed with 1 column volume of 10 mM trometamol, 110 mM sodium chloride, 2 mM calcium chloride, pH8.0. The column outlets were closed. Water was then circulated through the column jackets at 15°, 23°, and 26° C.

After 65 hours, circulation of water was stopped. The medium was washed with 10 mM trometamol, 110 mM sodium chloride, pH8.0 to recover the thrombin generated during the incubation. The results are shown in Table 2.

TABLE 2

| Column | Incubation temperature, ° C. | Thrombin clotting activity | |
|---|---|---|---|
| | | Total recovered, iu | Total > 2000 iu/mg, iu |
| 1 | 15 | 864,000 | 423,000 |
| 2 | 23 | 756,000 | 284,000 |
| 3 | 26 | 800,000 | 128,000 |

EXAMPLE 6

Trometamol Buffers and Incubation at Room Temperature for 16, 40 and 64 Hours 248 g of solvent-detergent treated prothrombin complex was diluted with 523 g of water to reduce its conductivity from 26.9 mS/cm to 9.33 mS/cm. The solution was then titrated to pH8.0. About 195 g of this solution was loaded onto each of three 1 cm diameter column packed with a 13 cm high bed of DEAE Sepharose CL6B, equilibrated with 10 mM trometamol, 110 mM sodium chloride, pH8.0. After loading each column, the medium was washed with 10 column volumes of 10 mM trometamol, 110 mM sodium chloride, pH8.0 to remove the solvent detergent reagents and weakly bound protein. The medium was then washed with 1 column volume of 10 mM trometamol, 110 mM sodium chloride, 5 mM calcium chloride, pH8.0. The column outlets were closed. The columns were stored at room temperature.

The three columns were stored for 16 hours, 40 hours, and 64 hours. At the end of each incubation the medium was washed with 10 mM trometamol, 110 mM sodium chloride, pH8.0 to recover the thrombin generated during the incubation. The results are shown in Table 3.

TABLE 3

| Column | Incubation, hours | Thrombin clotting activity | |
|---|---|---|---|
| | | Total recovered, iu | Total > 2000 iu/mg, iu |
| 1 | 16 | 30,700 | 0 |
| 2 | 40 | 407,000 | 197,000 |
| 3 | 64 | 500,000 | 158,000 |

EXAMPLE 7

Mechanism of Thrombin Generation

Experiments were performed to determine the mechanism of prothrombin activation to thrombin in the process of the invention.

Materials
Purified virus-inactivated prothrombin
Purified virus-inactivated factor X
Virus-inactivated antithrombin The prothrombin and factor X had been inactivated by solvent and detergent treatment using tri-n-butyl phosphate and polysorbate 80. The antithrombin had been virus-inactivated by heat-treatment.

Method

Three chromatography columns were packed with DEAE Sepharose CL-6B anion-exchange gel and equilibrated in trometamol-NaCl buffer. The three columns were then used as described in Table 4, and the products then tested for thrombin activity.

TABLE 4

| Column 1 | Column 2 | Column 3 |
|---|---|---|
| Load prothrombin | Load Factor X | Load Factor X |
| Equilibration | Equilibration | Equilibration |
| Buffer Wash | Buffer Wash | Buffer Wash |
| Calcium buffer incubation | Calcium buffer incubation | Calcium buffer incubation |
| Equilibration | Equilibration | Equilibration |
| Buffer Elution | Buffer Wash | Buffer Wash |
| | Load prothrombin | Load Antithrombin |
| | Equilibration | Equilibration |
| | Buffer Elution | Buffer Wash |
| | | Load prothrombin |
| | | Equilibration |
| | | Buffer Elution |

The results are shown in Table 5.

TABLE 5

| | Column 1 | Column 2 | Column 3 |
|---|---|---|---|
| Total Prothrombin loaded, iu | 2039 | 2044 | 2061 |
| Total Factor X loaded applied, u | 0 | 1222 | 1196 |
| Antithrombin applied, u | 0 | 0 | 850 |
| Thrombin generated, iu per iu prothrombin | <0.07 | 113 | <0.07 |

The results show that thrombin cannot be generated from virus-inactivated prothrombin exclusively by calcium (Column 1). Thrombin can be generated from virus-inactivated prothrombin by incubation with virus-inactivated factor X which has previously been incubated with calcium and the calcium is then removed before prothrombin contact (Column 2). Thrombin cannot be generated from virus-inactivated prothrombin by incubation with virus-inactivated factor X which has previously been incubated with calcium, if the factor X/factor Xa is then inactivated with antithrombin and both calcium and antithrombin are removed before prothrombin contact (Column 3).

The mechanism of thrombin generation in the process of the invention requires factor X to be activated by calcium and the prothrombin to then be activated to thrombin by the action of activated factor X (i.e. factor Xa), rather than directly by the calcium. Isolated prothrombin is not therefore a suitable starting material for use in the process of the invention.

EXAMPLE 8

Lack of Thrombin Generation Using Only Purified Prothrombin and Calcium

Prothrombin (Factor II) was separated from other prothrombin complex clotting factor proteins after virucidal treatment with solvent and detergent, by passage through a copper-charged Chelating Sepharose column.

This protein solution was either used in the presence of the co-purifying solvent and detergent reagents (SD), or was separated from the solvent and detergent reagents by re-chromatography on DEAE Sepharose anion-exchange gel.

The prothrombin in solution was incubated at pH 6.5 with 40 mM calcium chloride buffer at 25° C. for 3 hours. Thrombin activity was then measured.

The results are shown in Table 6.

TABLE 6

| Samples | Thrombin activity after 3 hours, iu/ml |
| --- | --- |
| Prothrombin with SD | less than 0.05 |
| Prothrombin after removal of SD | less than 0.05 |

The results confirm that isolated human prothrombin was not converted into thrombin by the action of calcium ions alone after undergoing a solvent-detergent virus inactivation procedure, regardless of whether the SD reagents were removed or not before addition of the calcium ions. Isolated prothrombin is not therefore a suitable starting material to use in the process of the invention.

EXAMPLE 9

Lack of Thrombin Generation by Calcium Action on Prothrombin Complex During or After Treatment with Solvent-Detergent Reagents Samples of three different prothrombin complex concentrates (containing factors II, IX and X) were incubated with 20 mM calcium chloride in solution and assayed for thrombin activity after incubation for 3 hours and 5 hours.

The prothrombin complex (PCC) samples derived from human plasma were:
A: PCC eluate from anion-exchange chromatography of CPS.
B: PCC eluate containing 1% polysorbate 80 detergent and 0.3% tri-n-butyl phosphate (TNBP) solvent.
C: solvent-detergent-treated PCC from which the solvent-detergent had been removed.

None of the prothrombin complex materials used in these experiments were activated during their manufacture, either intentionally or unintentionally, as determined by the NAPTT and FCT tests for activated clotting factors.

The results are shown in Table 7.

TABLE 7

| Sample | Thrombin after 3 hours, iu/ml | Thrombin after 5 hours, iu/ml |
| --- | --- | --- |
| A | 619 | 1168 |
| B | less than 1 | 3.48 |
| C | less than 1 | 2.02 |

The results show that negligible thrombin was generated from (non-activated) prothrombin complex in solution after it had been treated with solvent-detergent regardless of whether the solvent-detergent remained in the preparation at the time of incubation with calcium (compare the results for sample A with those for samples B and C). This confirmed the prior art teaching that calcium alone was not sufficient to activate solvent-detergent treated prothrombin complex. It is an essential feature of the process of the invention that the solvent-detergent treated prothrombin containing material is loaded onto an anion exchange medium in order for thrombin to be generated.

EXAMPLE 10

Activation with Calcium or Magnesium Ions 249 ml of solvent-detergent treated prothrombin complex was diluted with 150 ml deionised water to reduce its conductivity to 16 mS/cm. The solution was then titrated to pH8.0 with 1 M sodium hydroxide. 82 to 87 g of this solution was loaded onto each of three 1 cm diameter columns, each packed with 10 ml of DEAE Sepharose CL6B, equilibrated with 8 mM citrate, 10 mM phosphate, 137 mM sodium chloride, pH8.0. After loading, the medium was washed with 10 column volumes of 8 mM citrate, 10 mM phosphate, 137 mM sodium chloride, pH8.0 to remove the solvent detergent reagents and weakly bound protein. The medium was then washed with 1 column volume of activation buffer, either 8 mM citrate, 10 mM phosphate, 129 mM sodium chloride, 2 mM calcium chloride, pH8.0 (column 1) or 8 mM citrate, 10 mM phosphate, 129 mM sodium chloride, 2 mM magnesium chloride, pH8.0 (column 2) or 8 mM citrate, 10 mM phosphate, 129 mM sodium chloride, 2 mM calcium chloride, 2 mM magnesium chloride, pH8.0 (column 3). The column outlets were closed. The columns were stored at room temperature.

After about 64 hours, the medium was washed the activation buffer to recover the thrombin generated during the incubation. The results are shown in Table 8.

TABLE 8

| Column | Total thrombin chromogenic activity recovered | Metal Ion in Activation Buffer |
| --- | --- | --- |
| 1 | 178,000 iu | Calcium |
| 2 | 66,500 iu | Magnesium |
| 3 | 256,000 iu | Calcium/magnesium |

EXAMPLE 11

Formulation

Virus filtered thrombin solution prepared as in Example 1 was formulated to 10 mM trometamol, 200 mM NaCl, 40 mM $CaCl_2$, 2% sucrose, pH7.0 and potency adjusted to about 500 iu thrombin clotting activity/ml.

5 ml of this solution was dispensed into glass vials and freeze-dried. The freeze-dried material was heat-treated at 80° C. for 72 hours. In 3 runs an average recovery of 98% of the thrombin clotting activity was achieved across freeze-drying and an average of 98% across heat-treatment.

EXAMPLE 12

Formulation

Thrombin solution was formulated at approximately 1250 iu clotting activity/ml. All formulations contained 10 mM trometamol and 200 mM sodium chloride at pH 7.0. Additionally, they contained the added components shown below. The solutions were filled into vials, 2 ml per vial. The vials were freeze-dried and dry heat treated at 80° C. for 72 hours. The vials were then reconstituted with water and assayed to determine thrombin activity. Thrombin activity was compared with thrombin activity in samples taken before freeze-drying. The results are shown in Table 9.

TABLE 9

| [Calcium chloride], mM | Additional components | Recovery of clotting activity across freeze-drying and heat-treatment |
|---|---|---|
| 2 | — | 59% |
| 10 | — | 69% |
| 40 | — | 88% |
| 2 | 1% sucrose | 88% |
| 2 | 2% sucrose | 93% |
| 2 | 1% trehalose | 98% |
| 2 | 1% raffinose | 88% |
| 2 | 1% human albumin | 60% |
| 2 | 1% PEG 4000 | 78% |

The results showed that the conventional albumin stabiliser did not provide stability across freeze-drying and heat-treatment. Other combinations of calcium and carbohydrate gave improved stability across freeze-drying and heat-treatment.

EXAMPLE 13

Thrombin Formulation, Freeze Drying and Heat-Treatment

Thrombin solution was formulated at 500 iu/ml (5 ml fill). All formulations also contained 10 mM trometamol and 200 mM sodium at pH 7.0 and additionally contained the components shown below. The solutions were filled into vials, 5 ml per vial. The vials were freeze-dried and dry heat treated at 80° C. for 72 hours or 100° C. for 24 hours. The vials were then reconstituted with water and assayed to determine thrombin activity. Thrombin activity was compared with thrombin activity in samples taken before freeze-drying. The results are shown in Table 10.

TABLE 10

| [Calcium chloride], mM | Additional components | Fill volume, ml | Recovery of clotting activity across freeze-drying and heat-treatment | |
|---|---|---|---|---|
| | | | 80° C./72 hours | 100° C./24 hours |
| 2 | 2% sucrose | 5 | 79% | — |
| 40 | 2% sucrose | 5 | 97% | 89% |
| 2 | 1% trehalose | 5 | 92% | 73% |

The results showed that the optimum formulation was 10 mM trometamol and 200 mM sodium at pH 7.0 plus 40 mM calcium chloride and 2% sucrose.

EXAMPLE 14

Preparation of Thrombin 1.17 kg of solvent-detergent treated prothrombin complex was diluted with 2.58 kg of water to reduce its conductivity from 27.5 mS/cm to 9.12 mS/cm. The solution was then titrated to pH8.0 with 0.5 M sodium hydroxide. This solution was loaded onto a 5 cm diameter jacketed column packed with a 13 cm high bed of DEAE Sepharose CL6B, equilibrated with 10 mM trometamol, 110 mM sodium chloride, pH8.0. After loading the medium was washed with 15 column volumes of 10 mM trometamol, 110 mM sodium chloride, pH8.0 to remove the solvent detergent reagents and weakly bound protein. The medium was then washed with 1 column volume of 10 mM trometamol, 110 mM sodium chloride, 2 mM calcium chloride, pH8.0. The column outlets were closed. Water at 20° C. was circulated through the column jacket.

After 64 hours, circulation of water was stopped. The medium was washed with 10 mM trometamol, 110 mM sodium chloride, pH8.0 to recover the thrombin generated during the incubation. The first 4 column volumes of column effluent contained 4.3 million international units (iu) of thrombin clotting activity with a specific clotting activity of less than 2000 iu/mg total protein. The next 9 column volumes of effluent which contained 2.2 million iu clotting activity at a specific activity of 2100 iu/mg was frozen at −40° C. and kept for further processing.

900 g of the frozen eluate was thawed and filtered using a Planova 15N virus filter that had been equilibrated with 10 mM trometamol, 110 mM sodium chloride, pH8.0. There was a measured recovery of 95% of the thrombin clotting activity across freeze/thaw and 102% across virus filtration.

The filtrate was then formulated to 10 mM trometamol, 200 mM sodium chloride, 40 mM calcium chloride, 2% sucrose, by addition of a suitable buffer. The solution was diluted to an estimated thrombin clotting activity concentration of 550 iu/ml with 10 mM trometamol, 200 mM sodium chloride, 40 mM calcium chloride, 2% sucrose, pH7.0, and then titrated with 0.5 M hydrochloric acid to pH7.0.

This solution was then filtered through a 0.2 μm sterilising filter and then filled into vials, 5 g of solution per vial. The vials were freeze-dried and then dry-heat treated at 80° C. for 72 hours. There was a measured 97% recovery of the thrombin clotting activity across sterilising filtration, 102% across lyophilisation and 100% across dry-heat treatment.

EXAMPLE 15

Incubation Times 150 ml of solvent-detergent treated prothrombin complex was diluted with water to reduce the conductivity to approximately 9.3 mS/cm. The solution was then titrated to pH8.0. This quantity was loaded on to each of four columns packed with 12.5-12.9 mL of DEAE Sepharose CL6B, which had been equilibrated with 10 mM trometamol, 110 mM sodium chloride pH8.0. The columns were then washed with the same buffer to remove solvent-detergent reagents and weakly bound protein. The columns were then washed with 10 mM trometamol, 110 mM sodium chloride, 2 mM calcium chloride pH8.0, the column outlets were closed and the columns were isolated at room temperature (approximately 20° C.) for periods between 35 and 85 hours. At the end of each period, one of the columns was washed with 10 mM trometamol, 110 mM NaCl pH8.0 to recover the thrombin generated. The results are shown in Table 11:

TABLE 11

| Column | Incubation (hours) | Thrombin clotting activity | |
|---|---|---|---|
| | | Total recovered (iu) | Total >2000 iu/mg (iu) |
| 1 | 35 | 229,344 | 144,751 |
| 2 | 45 | 267,860 | 144,463 |
| 3 | 65 | 289,359 | 128,578 |
| 4 | 85 | 266,844 | 101,687 |

There is a general trend of increasing yield (total units) but decreasing purity (units >2000 iu/mg) with increasing incubation time. A skilled person can choose the incubation time to give the most favourable balance between total yield and purity in any particular situation.

What is claimed is:

1. A method for the preparation of virus-inactivated thrombin comprising the steps of:
   (a) subjecting a solution comprising prothrombin and Factor X to a virus inactivation procedure, by adding solvent and detergent to said solution, wherein the solvent is tri-n-butyl phosphate (TNBP);
   (b) loading the product of step (a) onto an anion exchange medium wherein the prothrombin and Factor X bind to the anion exchange medium;
   (c) washing the anion exchange medium to remove TNBP and detergent; and
   (d) activating the Factor X on the anion exchange medium to form Factor Xa by addition of metal ions, wherein the Factor Xa then activates the prothrombin to yield thrombin.

2. The method according to claim 1, wherein the solution comprising prothrombin and factor X is a prothrombin complex.

3. The method according to claim 1, further comprising the step of
   (e) selectively eluting the thrombin from the anion exchange medium.

4. The method according to claim 3, further comprising the steps of
   (f) passing the product of step (e) through a filter which retains pathogens;
   (g) adding a divalent metal ion and a carbohydrate to the product of step (f), and
   (h) freeze-drying and heat-treating the product of step (g) to inactivate viruses.

5. The method according to claim 1, wherein step (d) is performed without addition of phospholipids.

6. A method for the preparation of virus-inactivated thrombin comprising the steps of:
   (a) subjecting a solution comprising factor X to a virus inactivation procedure, by adding solvent and detergent to said solution, wherein the solvent is TNBP;
   (b) loading the product of step (a) onto an anion exchange medium wherein the Factor X binds to the anion exchange medium;
   (c) washing the anion exchange medium to remove TNBP and detergent used for the virus inactivation procedure in step (a);
   (d) activating the factor X on the anion exchange medium to form factor Xa by addition of metal ions; and
   (e) loading virus-inactivated prothrombin onto the anion exchange medium such that the activated Factor Xa converts prothrombin to thrombin.

7. The method according to claim 6, further comprising the step of
   (f) selectively eluting the thrombin from the anion exchange medium.

8. The method according to claim 7, further comprising the steps of
   (g) passing the product of step (f) through a filter which retains pathogens;
   (h) adding a divalent metal ion and a carbohydrate to the product of step (g), and
   (i) freeze-drying and heat-treating the product of step (h) to inactivate viruses.

9. The method according to claim 6, wherein step (d) is performed without addition of phospholipids.

10. The method according to claim 1 or 6 wherein the metal ions are divalent metal ions.

11. The method according to claim 10 wherein the divalent metal ions are magnesium and/or calcium ions.

12. A method for the preparation of virus-inactivated thrombin comprising the steps of:
   (a) loading a solution comprising prothrombin and factor X onto an anion exchange medium; and
   (b) subjecting the prothrombin and factor X to a virus inactivation procedure by adding solvent and detergent to said prothrombin and factor X on the anion exchange medium, wherein the solvent is TNBP;
   (c) washing the anion exchange medium to remove the TNBP and detergent used for the virus inactivation procedure in step (b); and
   (d) activating the Factor X on the anion exchange medium to form Factor Xa by addition of metal ions, wherein the Factor Xa then activates the prothrombin to yield thrombin.

13. The method according to claim 12 wherein the metal ions are divalent metal ions.

14. The method according to claim 13 wherein the divalent metal ions are magnesium and/or calcium ions.

15. The method according to claim 12, further comprising the step of
   (e) selectively eluting the thrombin from the anion exchange medium.

16. The method according to claim 15, further comprising the steps of
   (f) passing the product of step (e) through a filter which retains pathogens;
   (g) adding a divalent metal ion and a carbohydrate to the product of step (f), and
   (h) freeze-drying and heat-treating the product of step (g) to inactivate viruses.

17. The method according to claim 12, wherein step (d) is performed without addition of phospholipids.

18. A method for the preparation of virus-inactivated thrombin comprising the steps of:
   (a) loading a solution comprising Factor X onto an anion exchange medium; and
   (b) subjecting the Factor X to a virus inactivation procedure by adding solvent and detergent to said Factor X on the anion exchange medium, wherein the solvent is TNBP;
   (c) washing the anion exchange medium to remove the TNBP and detergent used for the virus inactivation procedure in step (b);

(d) activating the Factor X on the anion exchange medium to form factor Xa by addition of metal ions; and (e) loading virus-inactivated prothrombin onto the anion exchange medium such that the activated Factor Xa converts prothrombin to thrombin.

19. The method according to claim 18 wherein the metal ions are divalent metal ions.

20. The method according to claim 19 wherein the divalent metal ions are magnesium and/or calcium ions.

21. The method according to claim 18, further comprising the step of (e) selectively eluting the thrombin from the anion exchange medium.

22. The method according to claim 21, further comprising the steps of (f) passing the product of step (e) through a filter which retains pathogens;

(g) adding a divalent metal ion and a carbohydrate to the product of step (f), and (h) freeze-drying and heat-treating the product of step (g) to inactivate viruses.

23. The method according to claim 18, wherein step (d) is performed without addition of phospholipids.

* * * * *